United States Patent
Mascitelli et al.

(10) Patent No.: US 7,331,943 B2
(45) Date of Patent: Feb. 19, 2008

(54) INJECTION NEEDLE FOR SCLEROTHERAPY

(76) Inventors: Alessandro Mascitelli, Via Dei Salici, 48-56025, Pontedera(PI) (IT); Gilberto Moretti, Piazza Ferrari, 5-44025, Massafiscaglia(FE) (IT); Paolo Romagnoli, Via Pioppa, 325-44100, Ferrara (IT)

( * ) Notice: Subject to any disclaimer, the term of this patent is extended or adjusted under 35 U.S.C. 154(b) by 450 days.

(21) Appl. No.: 10/473,880

(22) PCT Filed: Mar. 28, 2002

(86) PCT No.: PCT/EP02/03483

§ 371 (c)(1),
(2), (4) Date: Oct. 2, 2003

(87) PCT Pub. No.: WO02/078771

PCT Pub. Date: Oct. 10, 2002

(65) Prior Publication Data

US 2004/0116879 A1 Jun. 17, 2004

(30) Foreign Application Priority Data

Apr. 2, 2001 (IT) .................. VI2001A0076

(51) Int. Cl.
*A61M 5/32* (2006.01)
*A61M 5/00* (2006.01)
(52) U.S. Cl. .............. 604/272; 604/264; 604/239
(58) Field of Classification Search ........... 604/170.03, 604/185, 239–241, 264, 266, 272–274
See application file for complete search history.

(56) References Cited

U.S. PATENT DOCUMENTS

| 2,748,768 A | | 6/1956 | Huber | |
|---|---|---|---|---|
| 3,082,769 A | | 3/1963 | Palmer | |
| 3,828,767 A | * | 8/1974 | Spiroff | 600/435 |
| 4,699,612 A | * | 10/1987 | Hamacher | 604/506 |
| 5,478,328 A | * | 12/1995 | Silverman et al. | 604/272 |
| 5,662,619 A | * | 9/1997 | Zarate | 604/272 |
| 5,716,348 A | | 2/1998 | Marinacci et al. | 604/272 |
| 6,425,854 B1 | * | 7/2002 | Galt et al. | 600/29 |
| 6,443,929 B1 | * | 9/2002 | Kuracina et al. | 604/192 |

FOREIGN PATENT DOCUMENTS

| BE | 1 005 702 | 12/1993 |
|---|---|---|
| DE | 94 00 470 | 3/1994 |
| FR | 2 057 353 | 5/1971 |
| WO | 92 20389 | 11/1992 |
| WO | 96 31247 | 10/1996 |

* cited by examiner

*Primary Examiner*—Kevin C. Sirmons
*Assistant Examiner*—Andrew Gilbert

(57) ABSTRACT

An injection needle (1) particularly adapted for sclerotherapy is disclosed, comprising a cannula (2) with mainly longitudinal development defining a main axis (X), a duct (4) for passage of a sclerosing substance (L) to be injected into a vein (V) being defined inside said cannula. The duct (4) has at the lower end (2a) an inlet (5) for the sclerosing substance (L) and an outlet (6) for the sclerosing substance (L) at the upper end (2b). At lest a constriction (7) is provided inside the duct (4), one or more through holes (8, 9) made in the wall of the cannula (2) being provided upstream the constriction according to the direction of advancement of the sclerosing substance (L) along the duct (4).

9 Claims, 2 Drawing Sheets

INJECTION NEEDLE FOR SCLEROTHERAPY

The present invention relates to an injection needle particularly adapted to be used for sclerotherapy.

It is well known that the vascular system as a whole may be affected by several pathologies, many of which involving the venous system and its circulation; more particularly general reference may be made to varicose disorders or more precisely to varices that are a dilation of the surface venous blood stream involving piercing veins, especially of the lower limbs.

The main modifications of venous vessel are dilation, elongation and tortuosity of the vessel, loss of elasticity with increase of fibrous tissue, modification of thickness of the walls with disappearance or atrophy of valves and presence of thrombi.

The origin of said alterations seems to be the pathologic modification of the venous valving system.

In view of the foregoing and of the mentioned alterations the most important pathogenic moment is reached in the generation of the chronic venous insufficiency: edema, dystrophic skin complications, ulceration are the most apparent alterations to which ectasis of various severity, modification of the local temperature, slight blemish, trophic modifications should be added.

According to the known techniques in order to solve the above mentioned problems one may resort to surgery and/or a sclerotherapy treatment consisting in injecting into the vein the so called sclerosing substances causing a phlogistic reaction of the venous endothelium so as to cause a vein occlusion through a progressive formation of a thrombus.

The results published on the presently available anatomic pathologic works relating to the sclerosing therapy, lead to state that the mixed thrombus formed few hours after injection, is in contact with the vessel wall only at the points where there is a pathologic lesion of endothelium or intima, while there are free spaces where endothelium is preserved.

The phlebologist in order to obtain better clinical results in the sclerosing practice, should have at disposal one or more needles having the characteristic of injecting the sclerosing liquid inside the varices so as to wet the entire vessel circumference.

A limitation shown by the known needles consists in that the direction of the sclerosing liquid is generally longitudinal starting from the needle point with the drawback that the sclerosing agent does not contact the entire surface of the vein surrounding the needle but involves only 50%-60% of the inner surface of the vessel especially in case of injection of big veins.

The present invention aims at overcoming said drawback.

The main object of the invention is to provide a needle allowing to increase the area of contact of the liquid with the inner surface of the venous vessel to be treated.

Another object of the invention is to provide a needle having no difficulty of use in the clinical practice in comparison with use of needles of the prior art.

Said objects are attained by providing an injection needle more particularly for sclerotherapy that according to the contents of the main claim comprises a cannula with mainly longitudinal development defining a main axis, inside which a duct for passage of a sclerosing substance to be injected into the vein is defined, said duct having in a lower end an inlet for said sclerosing substance and at the upper end an outlet for said sclerosing substance, wherein inside said duct there is at least a constriction, one or more through holes made in the cannula wall being provided upstream said constriction according to the advancement direction of said sclerosing substance along said duct.

According to a preferred embodiment, the injection needle of the invention has only one constriction of the inner duct, arranged near the cannula outlet.

In proximity of the constriction and at the side facing the lower end of the cannula, two lateral through holes are made at opposite sides relative to the main axis, thus defining a longitudinal axis common to both holes arranged orthogonally to the main axis.

Advantageously the constriction of the inner duct of the cannula slows down the flow of the sclerosing substance upstream the constriction and allows to convey the substance along directions generally orthogonal to the direction defined by the needle axis.

Further features and advantages of the present invention will be apparent from the description of a preferred embodiment shown as an illustrative but non limiting example in the accompanying sheets of drawings in which.

Figure 1:
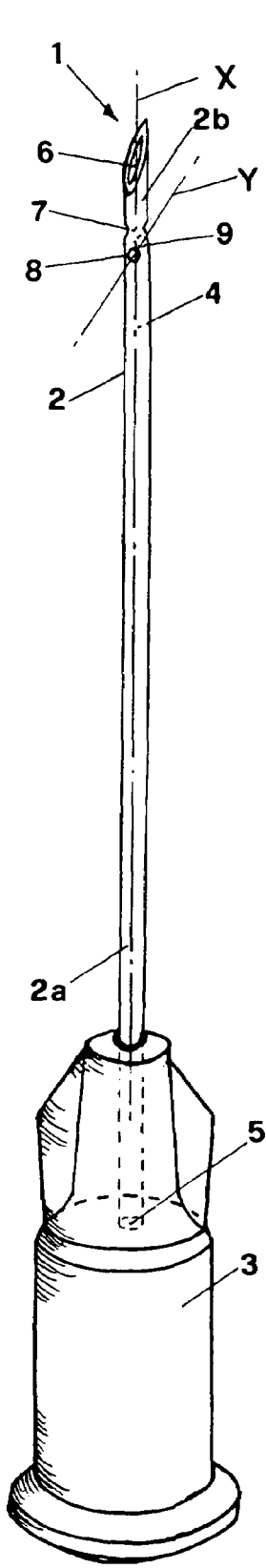
FIG. 1 is an isometric view of the needle of the invention.

The needle of the invention is shown in FIGS. 1 to 4 where it is generally indicated with reference numeral 1.

More particularly as shown in FIG. 1, the needle comprises a cannula 2 with a mainly longitudinal development according to the direction defined by the main axis X.

Figure 2:
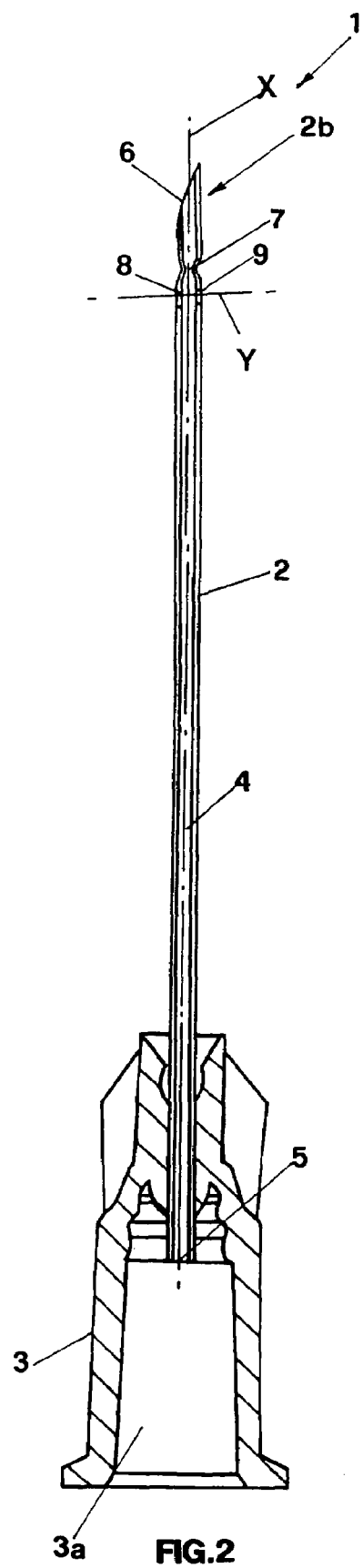
FIG. 2 is a sectional side view of FIG. 1.

The lower end 2a of cannula 2 is coupled to a barrel adapted to connect the needle 1 to means supplying the sclerosing substance L to be injected, such as for instance a syringe, a collection chamber 3a being defined in the barrel communicating with the inlet 5 of cannula 2 as shown more particularly in FIG. 2.

The upper end 2b of cannula 2 has a pointed shape obtained by sharpening the cannula 2 along an inclined plane adapted to allow the painless penetration of needle 1 into the skin for reaching the blood vessel V to be treated.

Cannula 2 is provided inside with a duct 4 connecting the inlet 5 arranged in proximity of the lower end 2a of cannula 2, to the outlet 6 arranged close to the upper end 2b of cannula 2.

Figure 3:
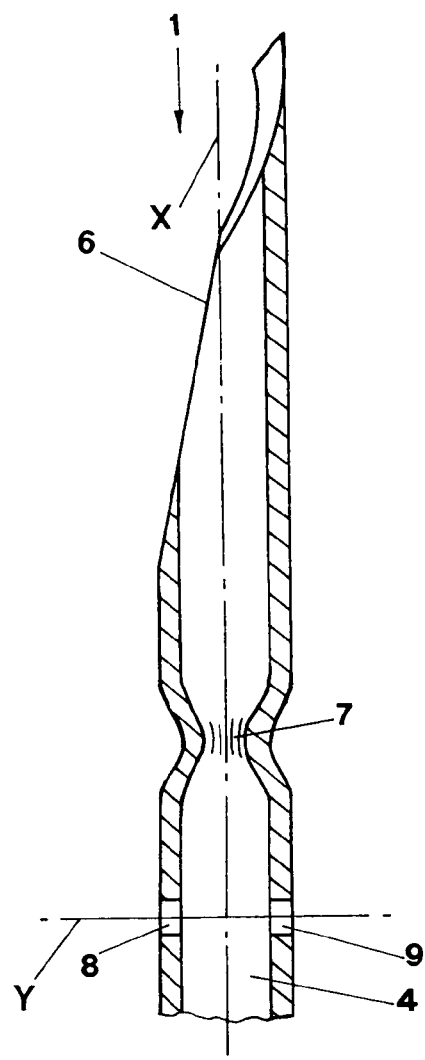
FIG. 3 is a sectional detail of FIG. 2.
Figure 4:
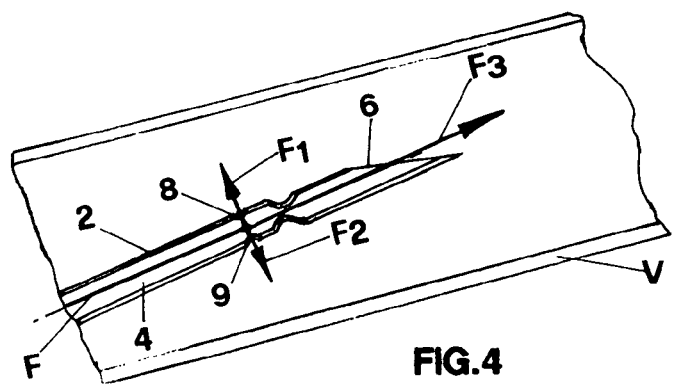
FIG. 4 shows the needle of the invention inserted in a blood vessel.

More particularly, as shown in FIG. 3, in proximity of the outlet 6, the inner duct 4 has a constriction 7 causing the duct 4 to narrow in the direction defined by the main axis X.

In proximity of the constriction 7 and at the opposite side relative to the outlet 6, two through holes 8, 9 are made in the wall of cannula 2.

These holes are arranged symmetrically and at either side relative to the main axis X defining a longitudinal axis Y arranged orthogonally to the said main axis X.

When the needle 1 is connected to the means supplying the sclerosing substance L to be injected through the barrel 3, the sclerosing substance L enters the collection chamber 3a, passes through the inlet 5 and runs through the inner duct 4 until it reaches the constriction 7. At this constriction 7 the sclerosing substance L undergoes a reduction of the flow rate in comparison with the inlet flow, indicated with F in FIG. 4, splitting into three secondary flows F1, F2, F3 having a greater velocity of the liquid flow than the velocity of the liquid through the duct 4.

More particularly the flow F3 concerns the outlet 6 of the needle 1 and the sclerosing substance L is being injected in a slightly inclined direction relative to the main axis X in view of the cannula sharpening, while flows F1 and F2 concern the side openings 8, 9 respectively.

In this way the sclerosing substance L reaches the inner surface of vessel V located laterally relative to the needle position, so as to touch a greater area of the inner wall of the blood vessel V.

From the foregoing it is therefore apparent that the injection needle in the embodiment herein shown and described, attains all the above mentioned intended objects.

In the constructional stage further constructional modifications neither described nor shown in the drawings may be made to the injection needle of the invention.

These constructional modifications may, for instance, consist of a different number and arrangement of the side openings or a different configuration and arrangement of the constriction inside the duct or again a different number of said constrictions.

In any event it is to be understood that said and further modifications or variations are to be intended covered by the present patent when falling within the scope of the inventive principle set forth in the appended claims.

The invention claimed is:

1. An injection needle for piercing the skin and entering the vein of a patient particularly adapted for sclerotherapy comprising:
   a cannula, including a tubular member having an outer wall and an inner wall, a first end and a skin piercing second end, and a central main axis extending therebetween, said cannula being formed with a central duct defined by said inner wall extending between the first and second ends, said duct having an inlet at the first end and an outlet at the second end, said inlet and outlet being in fluid communication through the duct for carrying a sclerosing substance to be injected into a vein along a flow direction between the inlet and the outlet;
   said inner wall having an inner diameter and a continuous circumferential deformation formed in the outer wall proximate to the second end of the duct, said deformation extending inwardly of the cannula forming a corresponding continuous circumferential constriction in the inner wall for reducing the inner diameter of the duct thereat;
   said outlet formed as a central opening along the central main axis at the second end of the duct and transverse thereto, and at least two through holes formed in the wall of the cannula upstream of and proximate to the constriction, said two through holes being disposed in the wall in a longitudinal direction on a plane orthogonal to said central main axis according to the flow direction of said flow direction of the sclerosing substance;
   said constriction causing die sclerosing substance to undergo a decrease in the flow through the duct and out of the central opening downstream of the constriction, and to increase the flow of the sclerosing substance through the two through holes upstream of the constriction.

2. The injection needle according to claim 1, wherein said two through boles arc formed in opposite sides relative to the central main axis.

3. The injection needle according to claim 1, wherein said central opening is arranged on an inclined plane relative to said central main axis.

4. The injection needle according to claim 1, wherein said first end of said cannula is coupled to a barrel connecting said needle to means for supplying said sclerosing substance, a collection chamber being defined in said barrel, and wherein said inlet leads into said collection chamber.

5. The injection needle according to claim 4, wherein said means for supplying the sclerosing substance comprises a syringe.

6. The injection needle according to claim 1 wherein said deformation is formed by roll forming the outer wall portion about its entire circumference.

7. The injection needle according to claim 1, wherein said through holes are formed by laser treatment.

8. An injection needle for piercing the skin and entering the vein of a patient particularly adapted for sclerotherapy comprising:
   a cannula having an outer wall and a inner wall with a selected diameter, said cannula having a longitudinal development defining a central main axis, a duct for passage of a sclerosing substance to be injected into a vein, said duct being defined inside said cannula. said duct having at a first end an inlet for said sclerosing substance and at a skin piercing second end outlet openings for the sclerosing substance, wherein a continuous circumferential deformation is formed in the outer wall of the duct forming a corresponding continuous circumferential constriction is provided inside said duct for reducing the diameter of the inner wall of the duct thereat and arranged proximate to said second end, said outlet openings including a first outlet opening located at the second end transverse of the central main axis, and at least two through holes formed in the wall of said cannula upstream said constriction according to a direction of advancement of said sclerosing substance along said duct, said at least two through holes defining a longitudinal direction disposed on a plane orthogonal to said central main axis, a barrel having a collection chamber, said barrel being coupled to the inlet at the first end of the needle for receiving the sclerosing substance from the collection chamber.

9. An injection needle for piercing the skin and entering the vein of a patient sclerotherapy comprising:
   a cannula being formed with a longitudinal development defining a central main axis, said cannula having a duct with an inner wall with a selected diameter and outer wall, said duct having an inlet end to a skin piercing outlet end for passage of a sclerosing substance to be injected into a vein in a flow direction from the inlet to the outlet, said inlet for receiving said sclerosing substance and an outlet for the sclerosing substance, a continuous circumferential deformation formed in the outer wall of the duct forming a continuous circumferential constriction formed inside said duct for reducing the diameter of the inner wall of the duct thereat and arranged proximate to said outlet end, said outlet including a first opening at the outlet end transverse to the central main axis. and at least two through holes formed in the wall of said cannula upstream of and proximate to said constriction according the flow direction of of said sclerosing substance along said duct, said at least two through holes defining a longitudinal direction on a plane orthogonal to said central main, axis, said constriction causing a reduction of the flow rate of the sclerosing substance at the outlet end and an increase of the flow of said sclerosing substance through said two through holes.

* * * * *

UNITED STATES PATENT AND TRADEMARK OFFICE
CERTIFICATE OF CORRECTION

PATENT NO. : 7,331,943 B2 Page 1 of 1
APPLICATION NO. : 10/473880
DATED : February 29, 2008
INVENTOR(S) : Allesandro Mascitelli et al.

It is certified that error appears in the above-identified patent and that said Letters Patent is hereby corrected as shown below:

Cover Page, item [73]
Assignee should read as follows: PENTAFERTE SPA, LOCALITA NOCELLA, CAMPLI (TE), ITALY Signed and Sealed this Twentieth Day of April, 2010

David J. Kappos
*Director of the United States Patent and Trademark Office*